United States Patent [19]

Steinman

[11] Patent Number: 5,674,201
[45] Date of Patent: Oct. 7, 1997

[54] ROTATABLE CATHETER HOUSED WITHIN A FLEXIBLE WING ASSEMBLY

[75] Inventor: Christopher P. Steinman, Sandy, Utah

[73] Assignee: Becton Dickinson and Company, Franklin Lakes

[21] Appl. No.: 405,166

[22] Filed: Mar. 16, 1995

[51] Int. Cl.⁶ ............................................. A61M 5/00
[52] U.S. Cl. .................. 604/165; 604/164; 604/174; 604/177; 604/264
[58] Field of Search ............................. 604/164, 165, 604/166, 174, 175, 177, 264, 283

[56] References Cited

U.S. PATENT DOCUMENTS

| | | | |
|---|---|---|---|
| 3,774,604 | 11/1973 | Danielsson | 604/169 |
| 3,826,256 | 7/1974 | Smith | 604/159 |
| 4,177,809 | 12/1979 | Moorehead | 128/214.4 |
| 4,362,156 | 12/1982 | Feller et al. | 604/165 |
| 4,710,175 | 12/1987 | Cartmell et al. | 604/177 |
| 4,747,831 | 5/1988 | Kulli | 604/110 |
| 4,834,718 | 5/1989 | McDonald | 604/195 |
| 4,994,034 | 2/1991 | Botich et al. | 604/110 |
| 5,085,639 | 2/1992 | Ryan | 604/177 X |
| 5,137,519 | 8/1992 | Littrell et al. | 604/174 |
| 5,163,913 | 11/1992 | Rantanen-Lee et al. | 604/177 |
| 5,267,971 | 12/1993 | Brimhall | 604/177 |
| 5,300,045 | 4/1994 | Plassche, Jr. | 604/263 |
| 5,304,144 | 4/1994 | Brimhall | 604/177 |
| 5,306,253 | 4/1994 | Brimhall | 604/165 |
| 5,312,337 | 5/1994 | Flaherty et al. | 604/175 X |
| 5,395,337 | 3/1995 | Clemens et al. | 604/110 |
| 5,505,711 | 4/1996 | Arakawa et al. | 604/177 X |

FOREIGN PATENT DOCUMENTS

| | | |
|---|---|---|
| 41 40 099 C1 | 5/1993 | Germany. |
| 2088721 | 6/1982 | United Kingdom. |
| WO 94/21319 | 9/1994 | WIPO. |
| WO 95/23003 | 8/1995 | WIPO. |

*Primary Examiner*—Sam Rimell
*Assistant Examiner*—Robert V. Racunas
*Attorney, Agent, or Firm*—Eric M. Lee, Esq.

[57] ABSTRACT

A winged IV catheter assembly includes a central tube having a proximal end and a distal end secured to a catheter. The outer circumference of the central tube has at least one annular bead. The assembly also includes a winged inserter having a longitudinally extending body and a pair of flexible wings connected to the body. The body includes a central passageway. The passageway includes at least one annular groove for receiving the annular bead on the central tube. The central tube and catheter can be rotatably positioned within the passageway of the winged inserter. The central tube and catheter then can be rotated with respect to the winged inserter as needed by a health care worker to facilitate insertion of the catheter into a patient.

10 Claims, 5 Drawing Sheets

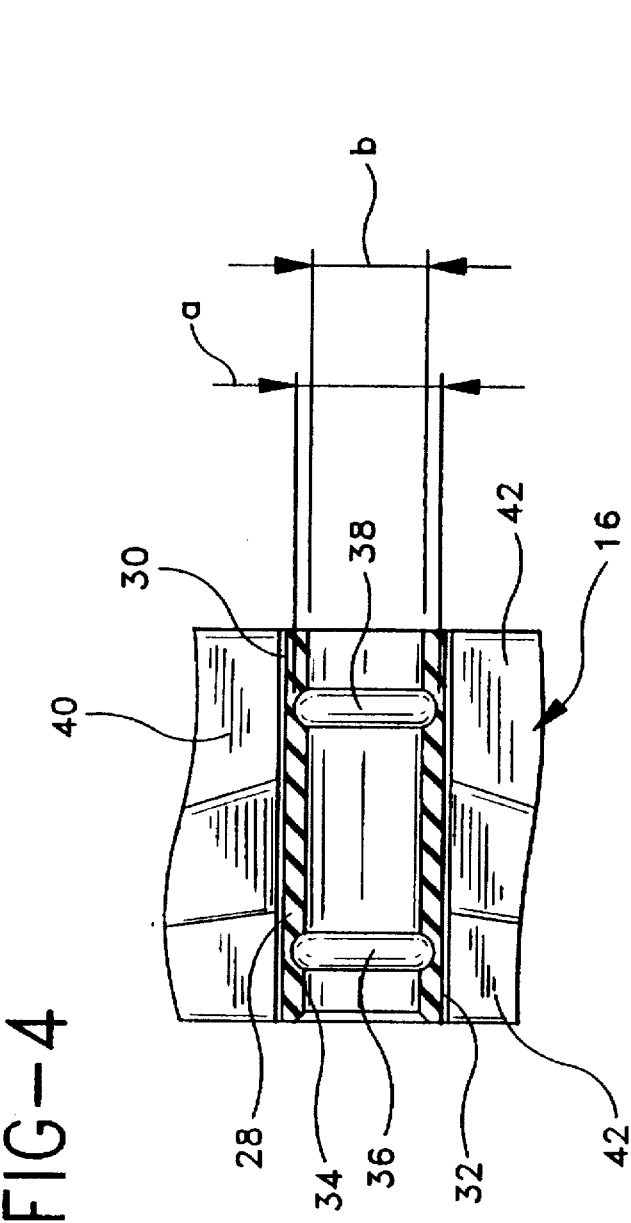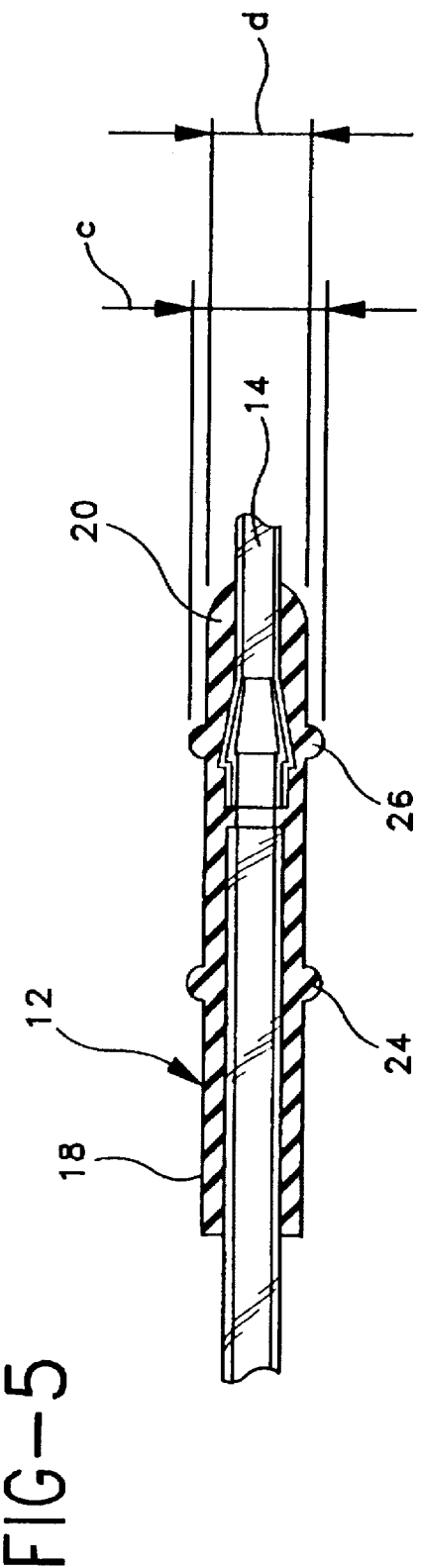

ROTATABLE CATHETER HOUSED WITHIN A FLEXIBLE WING ASSEMBLY

BACKGROUND OF THE INVENTION

This invention relates generally to winged intravenous (IV) catheter assemblies. The wings facilitate the handling of the catheter and needle during placement into a blood vessel. In addition, they provide a large surface area which can be taped against the patient's skin to ensure stability of the catheter at the venipuncture site. The wings are folded together to hold the needle axially in the catheter with the needle tip extended from the catheter in position for penetration into the vessel. After the catheter has been properly inserted, the needle may be withdrawn and the wings may be laid flat on the patient to enable the catheter to be adhesively taped to the skin of the patient.

Proper introduction of a winged IV catheter into a blood vessel can be difficult. Health care workers often finesse the distal end of the catheter into the proper position by slowly rotating the catheter about its longitudinal axis as the catheter is being advanced longitudinally. For example, health care workers may slowly rotate the catheter 180° in one direction and then slowly rotate the catheter 180° in the opposite direction while slowly advancing the catheter into the vein or artery. For winged IV catheter assemblies rotation of the catheter can be difficult in view of the wings projecting outwardly from the catheter. Even a small amount of rotation will urge a wing into the skin of the patient to prevent further rotation or will bias the catheter upwardly and away from the skin of the patient. Any such translation of the catheter is undesirable.

SUMMARY OF THE INVENTION

It is therefore an object of this invention to provide a winged IV catheter assembly that is easy to insert into a patient.

It is another object of this invention to provide a winged IV catheter assembly that allows the catheter to be rotated independently of the wings to facilitate insertion into a patient.

The winged IV catheter assembly of this invention includes a catheter subassembly and a winged inserter subassembly. It is to be understood that this invention may be used with an integral IV extension set. The proximal end of the catheter is securely and non-rotatably disposed in a central tube. Preferably, this central tube has an outside diameter of about 0.125 inches. The central tube includes an outer cylindrical surface with at least one circumferential discontinuity, such as an annular bead extending thereabout. Preferably two circumferential discontinuities or annular beads are spaced axially from one another on the outer surface of the central tube. Each annular bead is located about 0.10 inches from the end of the wing toward the center of the wing. In addition, each annular bead is preferably about 0.005 inches deep. The central tube and the circumferential discontinuity thereon may be unitarily molded from a plastic material. Additionally, at least the circumferential discontinuity of the central tube may be flexible. The central tube of the catheter subassembly is located inside the winged inserter subassembly.

The winged inserter subassembly includes an elongate body and a pair of flexible wings extending in opposite directions outwardly from the body. The body of the winged inserter is also flexible, and includes a passageway extending longitudinally therethrough. The winged inserter subassembly is made from a flexible thermoplastic material such as PVC or an elastomeric material such as silicone. The passageway is dimensioned to slidably and rotatably receive the central tube. Preferably the diameter of the passageway is about 0.130 inches. In particular, the passageway may have at least one circumferential discontinuity. The circumferential discontinuity may be an annular groove dimensioned and disposed to rotatably receive an annular bead or other such circumferential discontinuity on the central tube, as explained above.

The central tube and the elongate body are sized to permit the central tube to be slidably inserted into the passageway of the elongate body of the winged inserter subassembly. Resistance may be encountered as the circumferential discontinuity on the central tube contacts the body of the winged inserter. However, the flexible material in the central tube or winged inserter will permit further axial advancement of the central tube into the winged inserter. Sufficient longitudinal advancement of the central tube into the passageway will cause the circumferential discontinuity to effectively "snap" into the circumferential discontinuity of the winged inserter. Further axial movement of the central tube relative to the winged inserter will be resisted by the relative dimensional differences of the circumferential discontinuity on the central tube and portions of the passageway adjacent the circumferential discontinuity thereof. Thus the central tube is axially trapped in the passageway. However, the relative radial dimensions permit the central tube and the catheter connected thereto to be rotated freely and independently of the winged inserter. Preferably some interference is provided between the annular bead and mating annular groove to provide a small resistance to rotation and add stability to the assembly. Thus, the catheter can be separated from an inserter needle by rotating the catheter while holding the inserter needle stationary. Similarly, the central tube can be rotated as the catheter is being inserted into and advanced through a blood vessel.

In combination, the central tube and elongate body must be flexible and compressible enough to allow the needle extending through the assembly to be held in compression when the healthcare worker folds the wings together. This ensures sufficient force is exerted on the needle to keep it from sliding in a rearward direction during venipuncture. When the healthcare worker releases the wings, the needle is free to be removed and discarded.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numerals refer to like elements and in which:

FIG. 4 is a partial cross-sectional view of a portion of the winged inserter subassembly;

FIG. 5 is a partial cross-sectional view of the catheter subassembly; and

DETAILED DESCRIPTION OF THE PREFERRED EMBODIMENT

Figure 1:
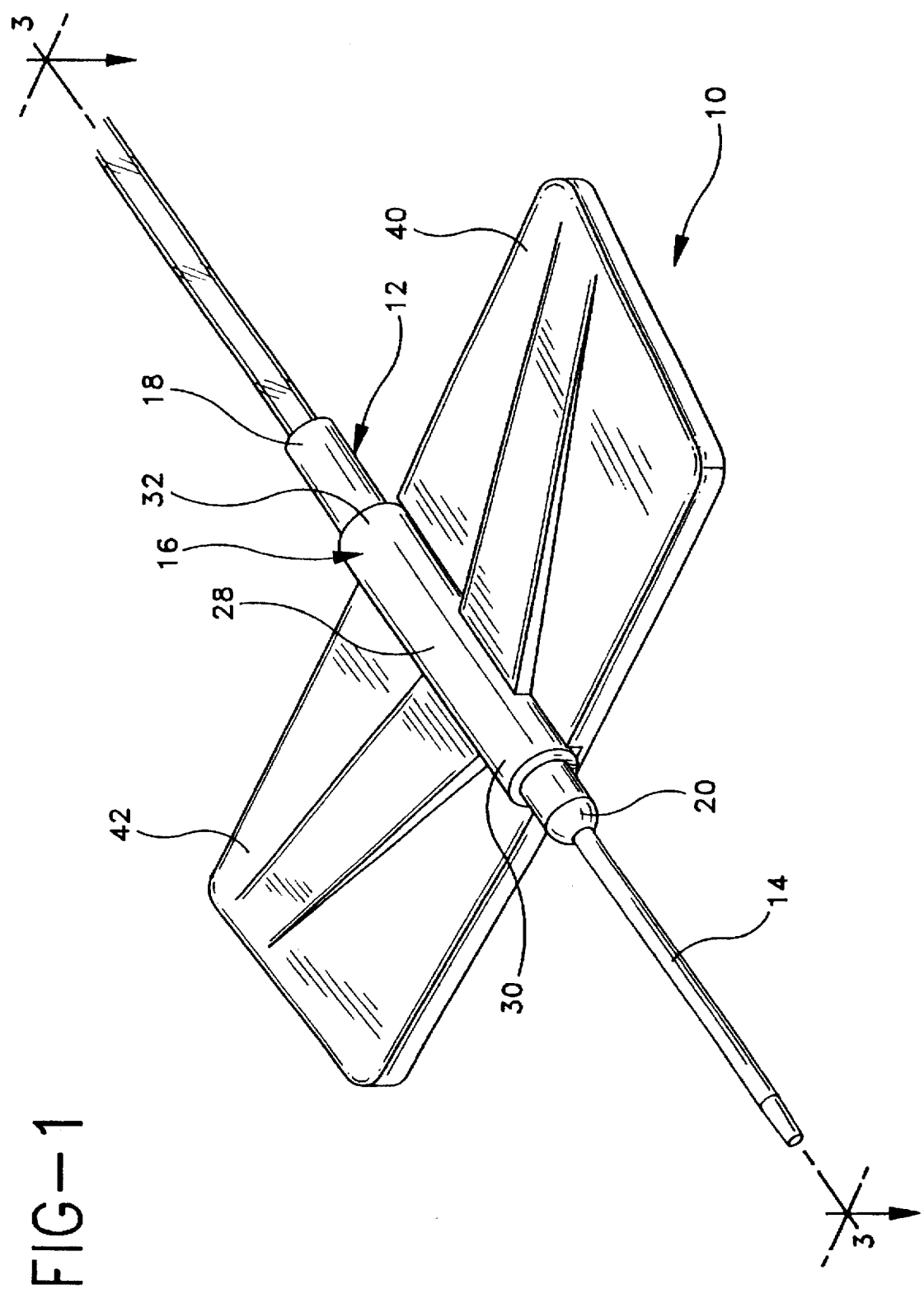
FIG. 1 is a perspective view of a winged IV catheter assembly in accordance with the subject invention.
Figure 2:
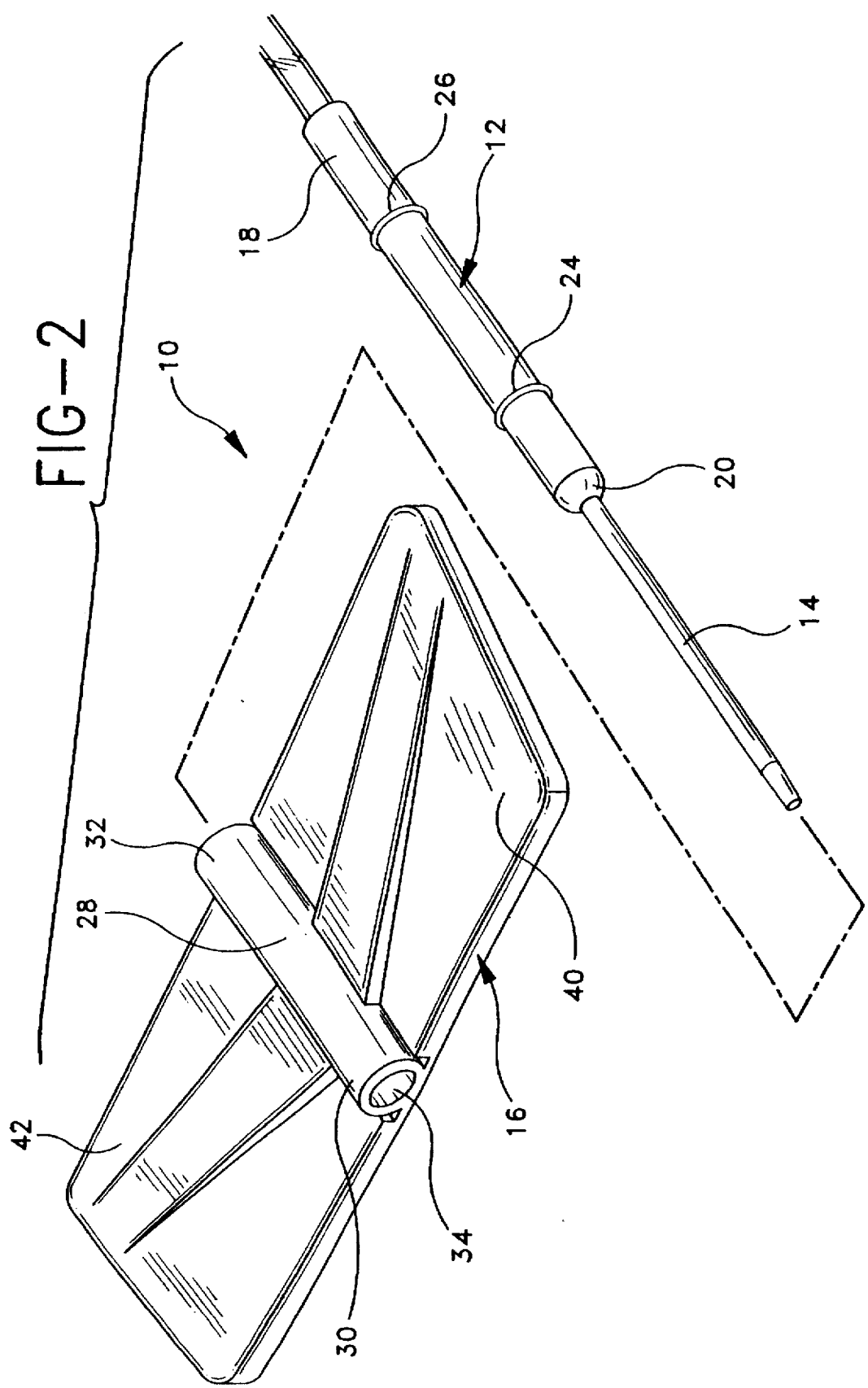
FIG. 2 is an exploded perspective view of the winged IV catheter assembly depicted in FIG. 1.
Figure 3:
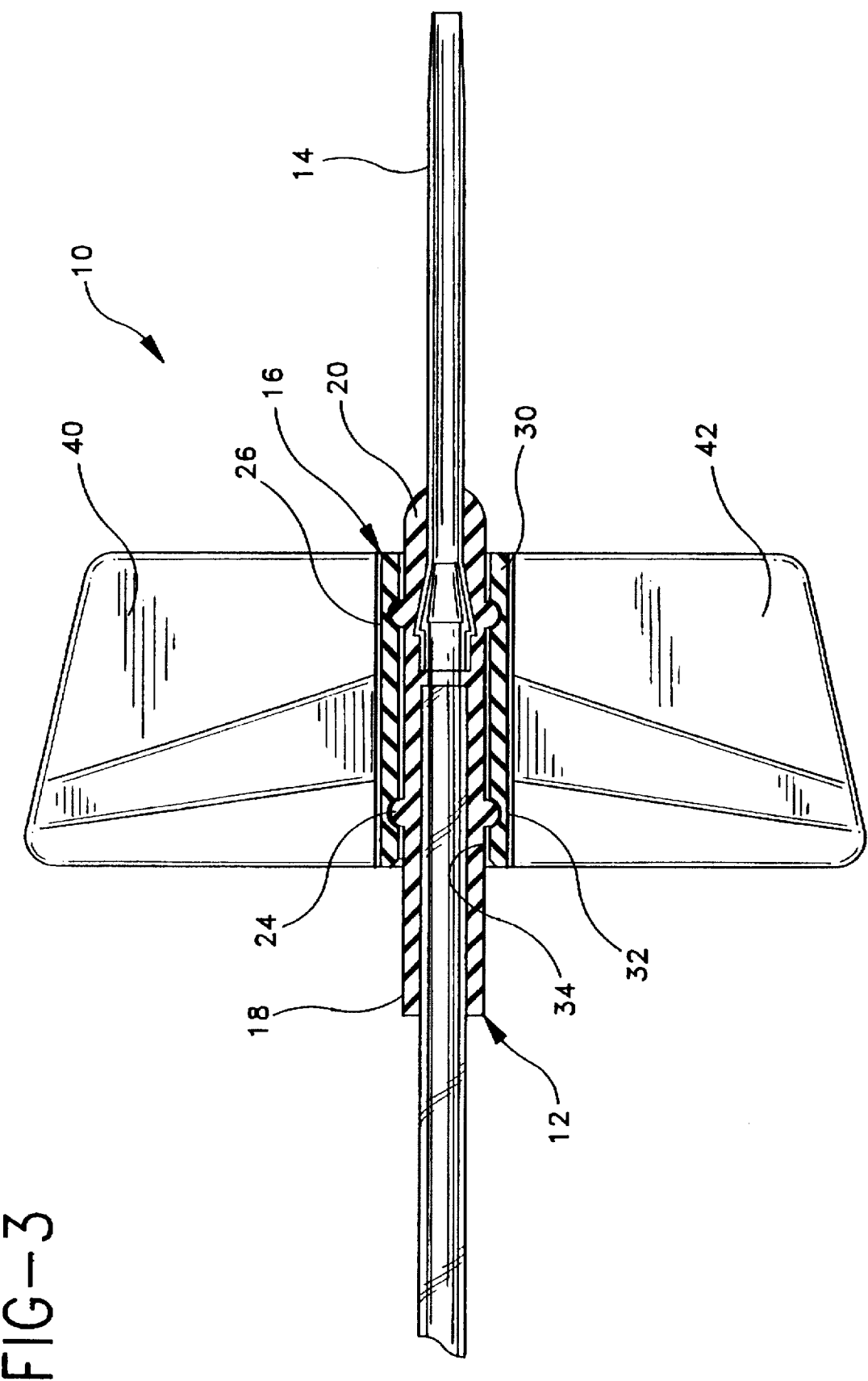
FIG. 3 is a top plan view partially in cross-section of the winged IV catheter assembly shown in FIG. 1.
Figure 6:
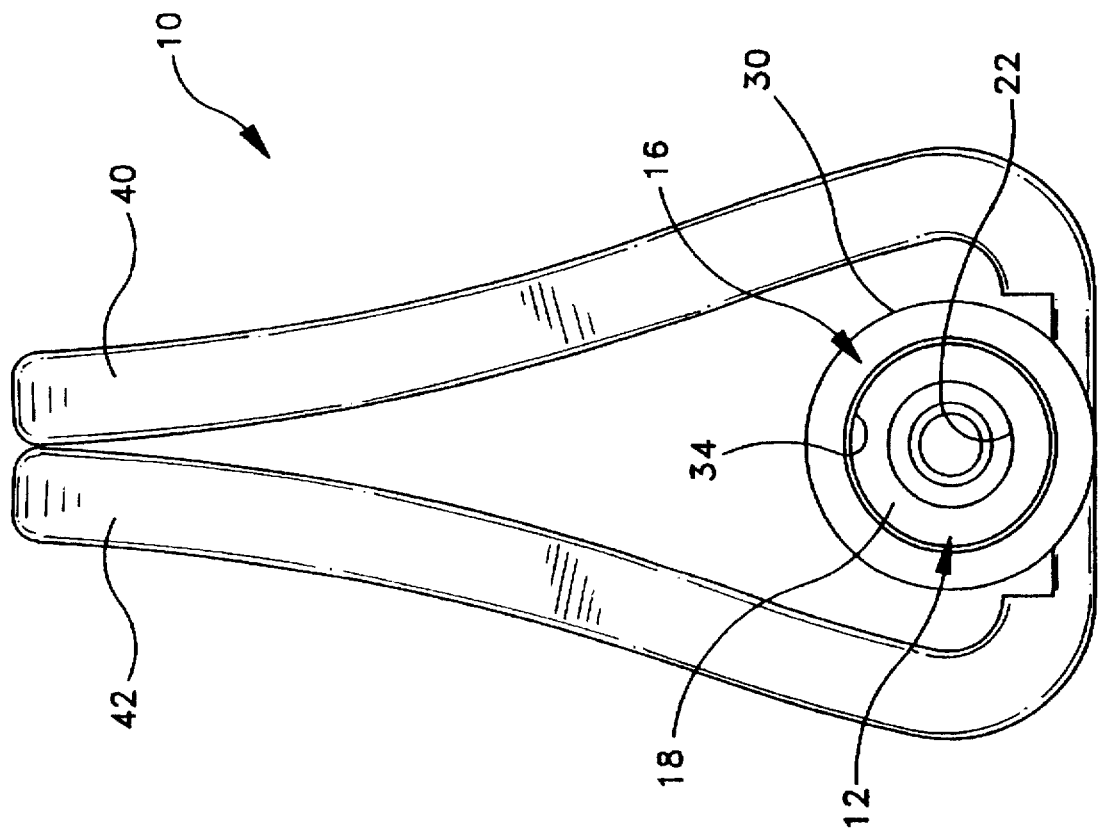
FIG. 6 is an end elevational view showing the winged IV catheter assembly of this invention with the wings folded together.

A winged IV catheter assembly in accordance with the subject invention is identified generally by the numeral 10 in FIGS. 1–3 and 6. Winged IV catheter assembly 10 includes a central tube 12, a catheter 14 securely, hermetically and rigidly affixed within central tube 12 and a flexible winged inserter 16.

Central tube 12 is an elongate tubular member unitarily molded from a moderately flexible plastic material such as a flexible PVC or a stiffer resin and should have a hardness in the range of Shore A 75–85 durometer. Central tube 12 includes opposed proximal and distal ends 18 and 20 respectively and a central passage 22 extending axially therethrough. Passage 22 is sized to allow an introducer needle (not shown), to pass therethrough. Distal end 20 of central tube 12 securely retains a proximal end of catheter 14 in rigid fluid tight and hermetic engagement. For example, catheter 14 may be securely retained in central tube 12 by available wedge technology using a mechanical interference fitment. Preferably a hollow, conical metal wedge is placed coaxially within catheter 14. The deformation to catheter 14 caused by the wedge snap fits into an internal recess in central tube 12 and ensures a secure and hermetic seal between catheter 14 and central tube 12.

With reference to FIG. 5, central tube 12 includes an outer cylindrical surface defining an outside diameter "d" along a major portion of the length of central tube 12. However, central tube 12 also is formed with annular beads 24 and 26 projecting unitarily outwardly therefrom at intermediate positions. Annular beads 24 and 26 define an outside diameter "c" which is greater than outside diameter "d" at other locations on central tube 12. Outside diameter "c" is preferably about 0.135 inches. Additionally, annular beads 24 and 26 are spaced axially from one another preferably by a distance of about 0.3 inches and are preferably about 0.10 inches from the ends of wings 40 and 42 when winged inserter 16 is fit on central tube 12.

Winged inserter 16 is unitarily molded from a flexible PVC or other flexible resin and should have a hardness in the range of Shore A 75–85 durometer. More particularly, winged inserter 16, as shown most clearly in FIGS. 3 and 4, includes an elongate central body 28 having opposed distal and proximal ends 30 and 32 respectively and a passageway 34 extending longitudinally therebetween. Proximal end 32 of body 28 may be chamfered to define a tapered entry into passageway 34. As shown most clearly in FIG. 4, passageway 34 defines an inside diameter "b" which is greater than outside diameter "d" of central tube 12, but slightly less than outside diameter "c" of annular beads 24 and 26 on central tube 12. Inside diameter "b" is preferably about 0.130 inches. Passageway 34 is characterized by annular grooves 36 and 38 which are axially spaced from one another preferably by a distance of about 0.3 inches and are preferably about 0.10 inches from the ends of wings 40 and 42. Annular grooves 36 and 38 each define an inside diameter "a" which is slightly less than outside diameter "c" of annular beads 24 and 26 of central tube 12. This slight interference fit provides some stability between central tube 12 and elongate central body 28.

Winged inserter 16 further includes a pair of flexible wings 40 and 42 projecting substantially diametrically in opposite directions from body 28. Wings 40 and 42 are thin and flexible and, in an unbiased condition, lie substantially in a common plane. However, wings 40 and 42 can be flexed and rotated toward one another such that surfaces of wings 40 and 42 will be in abutting face-to-face relationship with one another. The rotation of wings 40 and 42 toward one another ensures sufficient compressive force on the needle to keep it from sliding in a rearward direction during venipuncture. In addition, wings 40 and 42 effectively define a tab that can be easily gripped and manipulated by a health care worker using winged inserter 16.

Catheter assembly 10 is assembled by inserting catheter 14 and central tube 12 into passageway 34 of winged inserter 16. The chamfered entry to passageway 34 at proximal end 32 of winged inserter 16 may facilitate this initial entry. As noted above, central tube 12 defines an outside diameter "d" along most of its length that is slightly less than inside diameter "b" of passageway 34 along most of its length. Annular beads 24 and 26, on the other hand, each define an outside diameter "c" which is slightly greater than inside diameter "b" of passageway 34. Hence, resistance will be encountered during this portion of the insertion of central tube 12 into winged inserter 16. However, winged inserter 16 is formed from a flexible PVC or other flexible material and will yield in response to pressure exerted on central tube 12. Additionally, as noted above, central tube 12 also may be formed from a somewhat flexible material to facilitate assembly with winged inserter 16. Consequently continued insertion of central tube 12 into passageway 34 can be carried out without difficulty.

After sufficient insertion of central tube 12 in winged inserter 16, annular beads 24 and 26 will axially align with annular grooves 36 and 38 in passageway 34. This axial alignment will cause annular beads 24 and 26 to effectively "snap" into annular grooves 36 and 38. As noted above, annular beads 24 and 26 each define an outside diameter "c" which is slightly greater than inside diameters "a" on annular grooves 36 and 38. As a result, central tube 12 can be rotated with a slight amount of resistance within winged inserter 16. However, axial movement of central tube 12 and catheter 14 beyond the condition shown in FIGS. 1 and 3 can be carried out only with exertion of sufficient axial force to generate further dimensional deformities in body 28 of winged inserter 16 and/or in annular beads 24 and 26 on central tube 12.

Catheter assembly 10 can be introduced into a patient in substantially the conventional manner. The health care worker can hold wings 40 and 42 in face-to-face relationship with one another between the thumb and forefinger of one hand to insert catheter 14 into a patient and hold the needle in place during venipuncture. After catheter 14 has been properly inserted, the healthcare worker can release the wings and rotate central tube 12 to advance catheter 14 off of the introducer needle and into the patient.

Thus, it is seen that a winged IV catheter assembly is provided that is easy to insert into a patient and that allows the catheter to be rotated independently of the wings to facilitate insertion of the catheter into a patient.

What is claimed is:

1. A winged IV catheter assembly comprising:
   a winged inserter having an elongate body with opposed proximal and distal ends and a passageway extending axially therethrough defining an inner surface and having at least one circumferential groove with a first diameter formed on the inner surface;
   a central tube substantially axially fixed with respect to the winged inserter and rotatably disposed in the passageway and having a proximal end, a distal end and an outer surface extending therebetween, the outer surface including at least one circumferential protuberance thereon having a second diameter greater than the first diameter and being axially trapped by the circumferential groove in the passageway; and a catheter affixed to the distal end of the central tube whereby the catheter and the central tube can be rotated but cannot be substantially moved axially with respect to the winged inserter.

2. The winged IV catheter assembly of claim 1, wherein the winged inserter is formed from a flexible plastic material.

3. The winged IV catheter assembly of claim 2, wherein the flexible plastic material is a flexible PVC.

4. The winged IV catheter assembly of claim 1, wherein the central tube is formed from a plastic material.

5. The winged IV catheter assembly of claim 4, wherein the central tube is formed from a flexible plastic material.

6. A winged IV catheter assembly comprising:

a winged inserter unitarily molded from a flexible plastic material and having a longitudinally extending body with opposed proximal and distal ends and a passageway extending therebetween, said passageway having spaced apart cylindrical sections defining a first diameter and at least one intermediate section defining a second diameter;

an elongate catheter having opposed proximal and distal ends and an outside diameter smaller than the first and second diameters of the passageway; and a central tube having opposed proximal and distal ends, the distal end of the central tube being securely mounted on the proximal end of the catheter an outer surface extending between the proximal and distal ends of the central tube and having spaced apart cylindrical sections defining an outside diameter less than the first diameter of the passageway through the body of the winged inserter, the outer surface further having at least one intermediate section, the central tube being disposed in the passageway with the intermediate sections being radially aligned with one another such that the central tube and the catheter engaged therein are substantially axially fixed in the passageway and are rotatable relative to the winged inserter.

7. The winged IV catheter assembly of claim 6, wherein the winged inserter is molded from a flexible plastic material.

8. The winged IV catheter assembly of claim 7, wherein the central tube is molded from a plastic material.

9. The winged IV catheter assembly of claim 6, wherein the intermediate section of the passageway is an annular groove and the intermediate section of the central tube is an annular bead.

10. The catheter assembly of claim 9, wherein the passageway includes a pair of spaced apart annular grooves and the central tube includes a pair of annular beads rotatably disposed respectively in the groove.

* * * * *